United States Patent [19]

Müller et al.

[11] Patent Number: 6,159,992
[45] Date of Patent: Dec. 12, 2000

[54] FUNGICIDAL MIXTURES

[75] Inventors: Bernd Müller, Frankenthal; Hubert Sauter, Mannheim; Eberhard Ammermann, Heppenheim; Gisela Lorenz, Neustadt; Siegfried Strathmann, Limburgerhof; Maria Scherer, Landau; Klaus Schelberger, Gönnheim; Joachim Leyendecker, Ladenburg, all of Germany

[73] Assignee: BASF Aktiengesellschaft, Ludwigshafen, Germany

[21] Appl. No.: 09/242,715

[22] PCT Filed: Aug. 21, 1997

[86] PCT No.: PCT/EP97/04541

§ 371 Date: Feb. 22, 1999

§ 102(e) Date: Feb. 22, 1999

[87] PCT Pub. No.: WO98/08385

PCT Pub. Date: Mar. 5, 1998

[30] Foreign Application Priority Data

Aug. 30, 1996 [DE] Germany .............................. 196 35 079

[51] Int. Cl.[7] .......................... A01N 43/40; A01N 43/56; A01N 43/64
[52] U.S. Cl. ........................... 514/355; 514/383; 514/407
[58] Field of Search ..................... 514/383, 407, 514/355

[56] References Cited

U.S. PATENT DOCUMENTS 5,330,995  7/1994  Eicken et al. ............................ 514/355
5,438,070  8/1995  Eicken et al. ............................ 514/403

FOREIGN PATENT DOCUMENTS 2230140   3/1997   Canada .
4423613   1/1996   Germany .
96/01256  1/1996   WIPO .
96/01258  1/1996   WIPO .
96/03047  2/1996   WIPO .

Primary Examiner—Allen J. Robinson
Attorney, Agent, or Firm—Keil & Weinkauf

[57] ABSTRACT

The present invention relates to a fungicidal mixture which comprises a) a carbamate of the formula I

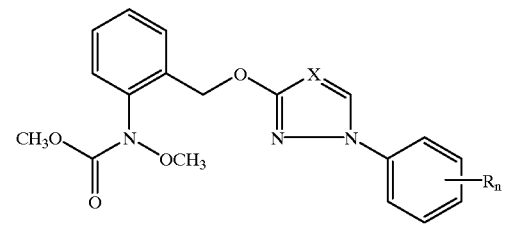

where X is CH and N, n is 0, 1 or 2 and R is halogen, $C_1$–$C_4$-alkyl and $C_1$–$C_4$-haloalkyl, it being possible for the radicals R to be different when n is 2, or a salt or adduct thereof, and b) an anilide of the formula II

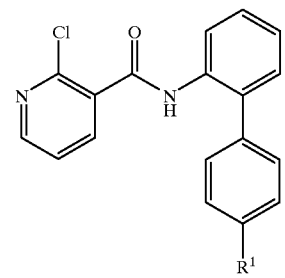

where $R^1$ is fluorine or chlorine, or a salt or adduct thereof, in a synergistically active amount.

13 Claims, No Drawings

FUNGICIDAL MIXTURES

This application is a 371 of PCT/EP97/04541, filed Aug. 21, 1997.

The present invention relates to a fungicidal mixture which comprises a) a carbamate of the formula I

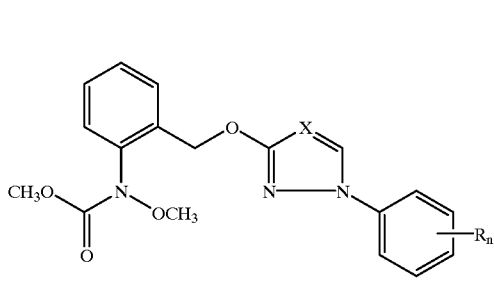

where X is CH and N, n is 0, 1 or 2 and R is halogen, $C_1$–$C_4$-alkyl and $C_1$–$C_4$-haloalkyl, it being possible for the radicals R to be different when n is 2, or a salt or adduct thereof, and b) an anilide of the formula II

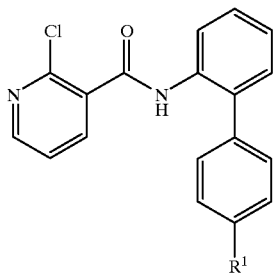

where $R^1$ is fluorine or chlorine, or a salt or adduct thereof, in a synergistically active amount.

Moreover, the invention relates to methods of controlling harmful fungi using mixtures of the compounds I and II and the use of the compound I and the compound II for the preparation of such mixtures.

The compounds of the formula I, their preparation and their action against harmful fungi are disclosed in the literature (PCT WO 96/01,256 and WO 96/01,258).

Also disclosed are the compounds II (EP-A 545 099, EP-A 589 301).

Moreover, DE Appl. No. 19 535 366.8 describes in general form synergistic mixtures which have fungicidal properties and which, on the one hand, comprise a respiration-inhibitory compound and, on the other hand, an anilide derivative of a general formula, which also embraces the compounds II according to the invention. The carbamates of the formula I according to the invention also have a respiration-inhibitory action; however, mixtures with carbamates are not described in DE Appl. No. 19 535 366.8

It was an object of the present invention to provide mixtures which have an improved activity against harmful fungi combined with a reduced total amount of active ingredient applied (synergistic mixtures) with a view to reducing the rate of application and improving the spectrum of action of the known compounds I and II.

Accordingly, we have found that this object is achieved by the mixture defined at the outset. Moreover, we have found that applying the compound I and the compound II simultaneously, ie. together or separately, or applying the compound I and the compound II in succession provides better control of the harmful fungi than is possible with the individual compounds alone.

Formula I represents, in particular, carbamates, in which the combination of the substituents corresponds to one line of the following table:

(I)

| No. | X | $R_n$ |
|---|---|---|
| I.1 | N | 2-F |
| I.2 | N | 3-F |
| I.3 | N | 4-F |
| I.4 | N | 2-Cl |
| I.5 | N | 3-Cl |
| I.6 | N | 4-Cl |
| I.7 | N | 2-Br |
| I.8 | N | 3-Br |
| I.9 | N | 4-Br |
| I.10 | N | 2-$CH_3$ |
| I.11 | N | 3-$CH_3$ |
| I.12 | N | 4-$CH_3$ |
| I.13 | N | 2-$CH_2CH_3$ |
| I.14 | N | 3-$CH_2CH_3$ |
| I.15 | N | 4-$CH_2CH_3$ |
| I.16 | N | 2-$CH(CH_3)_2$ |
| I.17 | N | 3-$CH(CH_3)_2$ |
| I.18 | N | 4-$CH(CH_3)_2$ |
| I.19 | N | 2-$CF_3$ |
| I.20 | N | 3-$CF_3$ |
| I.21 | N | 4-$CF_3$ |
| I.22 | N | 2,4-$F_2$ |
| I.23 | N | 2,4-$Cl_2$ |
| I.24 | N | 3,4-$Cl_2$ |
| I.25 | N | 2-Cl, 4-$CH_3$ |
| I.26 | N | 3-Cl, 4-$CH_3$ |
| I.27 | CH | 2-F |
| I.28 | CH | 3-F |
| I.29 | CH | 4-F |
| I.30 | CH | 2-Cl |
| I.31 | CH | 3-Cl |
| I.32 | CH | 4-Cl |
| I.33 | CH | 2-Br |
| I.34 | CH | 3-Br |
| I.35 | CH | 4-Br |
| I.36 | CH | 2-$CH_3$ |
| I.37 | CH | 3-$CH_3$ |
| I.38 | CH | 4-$CH_3$ |
| I.39 | CH | 2-$CH_2CH_3$ |
| I.40 | CH | 3-$CH_2CH_3$ |
| I.41 | CH | 4-$CH_2CH_3$ |
| I.42 | CH | 2-$CH(CH_3)_2$ |
| I.43 | CH | 3-$CH(CH_3)_2$ |
| I.44 | CH | 4-$CH(CH_3)_2$ |
| I.45 | CH | 2-$CF_3$ |
| I.46 | CH | 3-$CF_3$ |
| I.47 | CH | 4-$CF_3$ |
| I.48 | CH | 2,4-$F_2$ |
| I.49 | CH | 2,4-$Cl_2$ |
| I.50 | CH | 3,4-$Cl_2$ |
| I.51 | CH | 2-Cl, 4-$CH_3$ |
| I.52 | CH | 3-Cl, 4-$CH_3$ |

Especially preferred are the compounds I.12, I.23, I.32 and I.38.

Due to the basic character of the nitrogen atoms which they contain, the compounds I are capable of forming salts or adducts with inorganic or organic acids or with metal ions.

When providing the mixtures, it is preferred to employ the pure active ingredients I and II with which further active ingredients against harmful fungi or against other pests such as insects, arachnids or nematodes, or else herbicidally active ingredients, growth regulators or fertilizers, may be admixed.

The mixtures of the compounds I and II, or the simultaneous, joint or separate use of the compounds I and II, are distinguished by an outstanding activity against a wide spectrum of phytopathogenic fungi, in particular from the classes of the Ascomycetes, Basidiomycetes, Phycomycetes and Deuteromycetes. Some of them act systemically and can therefore also be employed as foliar- and soil-acting fungicides.

They are especially important for controlling a large number of fungi on a variety of crop plants such as cotton, vegetables (eg. cucumbers, beans, tomatoes, potatoes and cucurbits), barley, grass, oats, bananas, coffee, maize, fruit species, rice, rye, soya beans, grapevines, wheat, ornamentals, sugar cane, and a variety of seeds.

They are particularly suitable for controlling the following phytopathogenic fungi: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grapevines, Puccinia species in cereals, Rhizoctonia species in cotton, rice and lawns, Ustilago species in cereals and sugar cane, *Venturia inaequalis* (scab) in apples, Helminthosporium species in cereals, *Septoria nodorum* in wheat, *Botrytis cinerea* (gray mold) in strawberries, vegetables, ornamentals and grapevines, *Cercospora arachidicola* in groundnuts, *Pseudocercosporella herpotrichoides* in wheat and barley, *Pyricularia oryzae* in rice, *Phytophthora infestans* in potatoes and tomatoes, *Plasmopara viticola* in grapevines, Pseudocercosporella species in hops and cucumbers, Alternaria species in vegetables and fruit, Mycosphaerella species in bananas and Fusarium and Verticillium species.

Furthermore, they can be used in the protection of materials (eg. the protection of wood), for example against *Paecilomyces variotii*.

The compounds I and II can be applied simultaneously, ie. together or separately, or in succession, the order in the case of separate application generally not having any effect on the result of the control measures.

The compounds I and II are usually used in a weight ratio of 10:1 to 0.025:1, preferably 5:1 to 0.05:1, in particular 1:1 to 0.05:1.

The rates of application of the mixtures according to the invention are, especially in the case of agricultural land, from 0.01 to 8 kg/ha, preferably 0.1 to 5 kg/ha, in particular 0.5 to 3.0 kg/ha depending on the nature of the desired effect.

In the case of the compounds I, the rates of application are from 0.01 to 2.5 kg/ha, preferably 0.05 to 2.5 kg/ha, in particular 0.1 to 1.0 kg/ha.

Accordingly, in the case of the compounds II, the rates of application are from 0.01 to 10 kg/ha, preferably 0.05 to 5 kg/ha, in particular 0.05 to 2.0 kg/ha.

For seed treatment, the rates of application of the mixture are generally from 0.001 to 250 g/kg of seed, preferably 0.01 to 100 g/kg, in particular 0.01 to 50 g/kg.

If the control targets are phytopathogenic harmful fungi, the separate or joint application of the compounds I and II, or of the mixtures of the compounds I and II, is effected by spraying or dusting the seeds, the plants or the soils before or after sowing the plants or before or after plant emergence.

The fungicidal synergistic mixtures according to the invention, or the compounds I and II, can be formulated for example in the form of ready-to-spray solutions, powders and suspensions or in the form of highly concentrated aqueous, oily or other suspensions, dispersions, emulsions, oil dispersions, pastes, dusts, materials for spreading or granules, and applied by spraying, atomizing, dusting, spreading or pouring. The use form depends on the intended purpose; in any case, it should guarantee as fine and uniform a distribution as possible of the mixture according to the invention.

The formulations are prepared in a manner known per se, eg. by adding solvents and/or carriers. It is usual to admix inert additives such as emulsifiers or dispersants with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylaryl sulfonates, alkyl, lauryl ether and fatty alcohol sulfates, and salts of sulfated hexa-, hepta- and octadecanols or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenal ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for spreading and dusts can be prepared by mixing or jointly grinding the compounds I or II or the mixture of the compounds I and II with a solid carrier.

Granules (eg. coated granules, impregnated granules or homogeneous granules) are usually prepared by binding the active ingredient, or active ingredients, to a solid carrier.

Fillers or solid carriers are, for example, mineral earths such as silica gel, silicas, silicates, talc, kaolin, limestone, lime, chalk, bole, loess, clay, dolomite, diatomaceous earth, calcium sulfate, magnesium sulfate, magnesium oxide, ground synthetic materials, and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise 0.1 to 95% by weight, preferably 0.5 to 90% by weight, of one of the compounds I or II or of the mixture of the compounds I and II. The active ingredients are employed in a purity of from 90% to 100%, preferably 95% to 100% (according to NMR spectrum or HPLC.

The compounds I or II or the mixtures or the corresponding formulations are applied by treating the harmful fungi, their environment, or the plants, seeds, soils, areas, materials or spaces to be kept free from them with a fungicidally active amount of the mixture, or of the compounds I and II in the case of separate application.

Application can be effected before or after infection by the harmful fungi.

USE EXAMPLE

Activity Against *Botrytis cinerea*

The active ingredients, separately or together, were prepared as a 10% emulsion in a mixture of 70% by weight of cyclohexanone, 20% by weight of Nekanil® LN (Lutensol® AP6, wetting agents having emulsifying and dispersing action, based on ethoxylated alkylphenols) and 10% by weight of Emulphor® EL (Emulan® EL, emulsifier based on ethoxylated fatty alcohols) and diluted with water to give the desired concentration.

After 4–5 leaves had developed properly, bell pepper seedlings cv. "Neusiedler Ideal Elite" were sprayed to run-off with aqueous suspensions comprising 80% by weight of active ingredient and 20% by weight of emulsifier in the dry matter. After the spray coating had dried on, the plants were sprayed with a conidia suspension of the fungus *Botrytis cinerea* and placed into a chamber at high atmospheric humidity and 22–24° C. After 5 days, the disease had developed to such an extent on the untreated control plants that the resulting foliar necroses covered most of the leaves.

Evaluation was carried out by determining the infected leaf areas in percent. These percentages were converted into efficacies. The efficacy (W) was determined as follows, using Abbot's formula:

$$W=(1-\alpha)\cdot 100/\beta$$

$\alpha$ is the level of fungal infection of the treated plants in % and $\beta$ is the level of fungal infection of the untreated (control) plants in %

An efficacy of 0 means that the infection level of the treated plants corresponds to that of the untreated control plants; when the efficacy is 100, the treated plants are free from infection.

The expected efficacies of the mixtures of the active ingredients were determined using Colby's formula [R. S. Colby, Weeds 15, 20–22 (1967)] and compared with the observed efficacies.

Colby's formula: $E=x+y-x\cdot y/100$

E expected efficacy, expressed in % of the untreated control, when using the mixture of the active ingredients A and B at the concentrations a and b x efficacy, expressed in % of the untreated control, when using active ingredient A at a concentration of a y efficacy, expressed in % of the untreated control, when using active ingredient B at a concentration of b The synergistic effect of the mixtures according to the invention was shown by the following tests:

USE EXAMPLES

The tests ware carried out with the following compounds:

I.A corresponds to compound I.32 in the table on page 3 of the application

I.B corresponds to compound I.38 in the table on page 3 of the application

II.A see formula II in claim 1 where $R^1$ is chlorine

II.B see formula II in claim 1 where $R^1$ is fluorine

Use Example 1

Activity Against *Phytophthora infestans*

Leaves of plants cv. "Groβe Fleischtomate" in pots were sprayed to run-off with an aqueous suspension made with a stock solution of 10% of active ingredient, 63% of cyclohexanone and 27% of emulsifier. The next day, the leaves were infected with an aqueous zoospore suspension of *Phytophthora infestans*. The plants were subsequently placed into a water-vapor-saturated chamber at from 16 to 18° C. After 6 days, the tomato blight had developed on the untreated, but infected, control plants to such an extent that it was possible to determine the disease level visually in %.

The visually determined values for the percentage of diseased leaf area were converted to efficacies as % of the untreated control. An efficacy of 0 is the same disease level as in the case of the untreated control, an efficacy of 100 is a disease level of 0%. The expected efficacies for combinations of active ingredients were determined using Colby's formula (Colby, S. R. "Calculating synergistic and antagonistic responses of herbicide Combinations", Weeds, 15, 1967, pp. 20–22) and compared with the observed efficacies.

Untreated Control: Disease Level 88%

TABLE 1.1

Efficacy of the individual active ingredients

| Active ingredient | Concentration of active ingredient in the spray mixture in ppm | Efficacy in % of the untreated control |
|---|---|---|
| I.A | 3.1 | 55 |
| | 0.8 | 43 |
| | 0.2 | 21 |
| I.B | 3.1 | 55 |
| | 0.8 | 43 |
| | 0.2 | 21 |
| II.A | 3.1 | 0 |
| | 0.8 | 0 |
| | 0.2 | 0 |
| II.B | 3.1 | 0 |
| | 0.8 | 0 |
| | 0.2 | 0 |

TABLE 1.2

Efficacy of the mixture

| Active ingredient mixture | Observed efficacy | Expected efficacy*) |
|---|---|---|
| 3.1 ppm I.A + 3.1 ppm II.A Mixing ratio 1:1 | 89 | 55 |
| 0.8 ppm I.A + 0.8 ppm II.A Mixing ratio 1:1 | 77 | 43 |
| 0.2 ppm I.A + 0.2 ppm II.A Mixing ratio 1:1 | 66 | 21 |
| 3.1 ppm I.A + 3.1 ppm II.B Mixing ratio 1:1 | 97 | 55 |
| 0.8 ppm I.A + 0.8 ppm II.B Mixing ratio 1:1 | 83 | 43 |
| 0.2 ppm I.A + 0.2 ppm II.B Mixing ratio 1:1 | 43 | 21 |
| 0.2 ppm I.B + 0.2 ppm II.B Mixing ratio 1:1 | 53 | 21 |

*)calculated using Colby's formula

The results of the experiment reveal that, for all mixing ratios, the observed efficacy exceeds the efficacy calculated using Colby's formula.

Use Example 2

Activity Against *Botrytis cinerea* on Bell Pepper Fruits

Disks of green bell pepper fruits were sprayed to run-off with an aqueous preparation of active ingredient made with a stock solution of 10% of active ingredient, 63% of cyclohexanone and 27% of emulsifier. 2 hours after the spray coating had dried on, the fruit disks were inoculated with a spore suspension of *Botrytis cinerea* containing $1.7\times10^6$ spores per ml of a 2% strength Biomalz solution. The inoculated fruit disks were subsequently incubated for 4 days in humid chambers at 18° C. The botrytis level on the diseased fruit disks was evaluated visually.

The visually determined values for the percentage of diseased leaf area were converted to efficacies as % of the untreated control. An efficacy of 0 is the same disease level as in the case of the untreated control, an efficacy of 100 is a disease level of 0%. The expected efficacies for combinations of active ingredients were determined using the above-mentioned Colby's formula and compared with the observed efficacies.

Untreated Control: Disease Level 97%

TABLE 2.1

Efficacy of the individual active ingredients

| Active ingredient | Concentration of active ingredient in the spray mixture in ppm | Efficacy in % of the untreated control |
|---|---|---|
| I.A | 3.1 | 38 |
|  | 0.8 | 2 |
| I.B | 3.1 | 28 |
| II.A | 3.1 | 28 |
| II.B | 3.1 | 69 |
|  | 0.8 | 0 |

TABLE 2.2

Efficacy of the mixture

| Active ingredient mixture | Observed efficacy | Expected efficacy*) |
|---|---|---|
| 3.1 ppm I.A + 3.1 ppm II.A Mixing ratio 1:1 | 79 | 56 |
| 3.1 ppm I.B + 3.1 ppm II.A Mixing ratio 1:1 | 69 | 48 |
| 0.8 ppm I.A + 0.8 ppm II.B Mixing ratio 1:1 | 49 | 2 |
| 3.1 ppm I.B + 3.1 ppm II.B Mixing ratio 1:1 | 90 | 78 |

*)calculated using Colby's formula

The results of the experiment reveal that, for all mixing ratios, the observed efficacy exceeds the efficacy calculated in advance using Colby's formula.

Use Example 3

Activity Against *Botrytis cinerea* on Bell Pepper

After 4–5 leaves had developed properly, bell pepper seedlings cv. "Neusiedler Ideal Elite" were sprayed to run-off with an aqueous preparation of active ingredient made with a stock solution of 10% of active ingredient, 63% of cyclohexanone and 27% of emulsifier. The next day, the treated plants were inoculated with a spore suspension of *Botrytis cinerea* containing $1.7 \times 10^6$ spores/ml in a 2% strength aqueous Biomalz solution. The test plants were then placed into a controlled-environment cabinet at 22 to 24° C. and high atmospheric humidity. After 5 days, the extent of fungal disease on the leaves was determined visually in %.

The visually determined values for the percentage of diseased leaf area were converted to efficacies as % of the untreated control. An efficacy of 0 is the same disease level as in the case of the untreated control, an efficacy of 100 is a disease level of 0%. The expected efficacies for combinations of active ingredients were determined using the above-mentioned Colby's formula and compared with the observed efficacies.

Untreated Control: Disease Level 72%

TABLE 3.1

Efficacy of the individual active ingredients

| Active ingredient | Concentration of active ingredient in the spray mixture in ppm | Efficacy in % of the untreated control |
|---|---|---|
| I.A | 3.1 | 44 |
|  | 0.8 | 3 |
| I.B | 3.1 | 0 |
| II.A | 3.1 | 0 |
| II.B | 3.1 | 76 |
|  | 0.8 | 0 |

TABLE 3.2

Efficacy of the mixture

| Active ingredient mixture | Observed efficacy | Expected efficacy*) |
|---|---|---|
| 3.1 ppm I.A + 3.1 ppm II.A Mixing ratio 1:1 | 86 | 44 |
| 3.1 ppm I.B + 3.1 ppm II.A Mixing ratio 1:1 | 72 | 0 |
| 0.8 ppm I.A + 0.8 ppm II.B Mixing ratio 1:1 | 30 | 3 |
| 3.1 ppm I.B + 3.1 ppm II.B Mixing ratio 1:1 | 93 | 76 |

*)calculated according to Colby's formula

The results of the experiment reveal that, for all mixing ratios, the observed efficacy exceeds the efficacy calculated in advance using Colby's formula.

What is claimed is:
1. A fungicidal composition comprising
a) a carbamate I

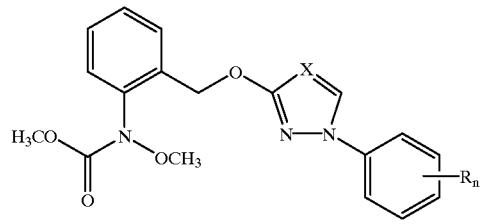

(I)

wherein X is CH, n is 0, 1 or 2, R is halogen, $C_1$–$C_4$-alkyl or $C_1$–$C_4$-haloalkyl, and the radicals R are identical or different when n is 2, or a salt or adduct thereof, and
b) an anilide II

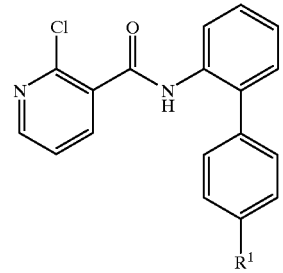

(II)

wherein $R^1$ is fluorine or chlorine, or a salt or adduct thereof, in a synergistically effective amount and a weight ratio of from 10:1 to 0.05:2.

2. The composition defined in claim 1, wherein the weight ratio of the carbamate I or the salt or adduct thereof to the anilide II is from 5:1 to 0.05: 1.

3. The composition of claim 1 which is conditioned in two parts, one part comprising the carbamate I in a solid or liquid carrier and the other part comprising the anilide II in a solid or liquid carrier.

4. The composition defined in claim 1, wherein the weight ratio of the carbamate I or the salt or adduct thereof to the anilide II is from 1:1 to 0.05:1.

5. A method for controlling harmful fungi, which comprises treating the harmful fungi, their environment, or plants, seeds, soils, areas, materials or spaces to be kept free from said fungi with synergistically effective amounts of the carbamate I set forth in claim 1 or a salt or adduct thereof and the anilide II as set forth in claim 1, in a weight ratio of from 10:1 to 0.05:2.

6. The method defined in claim 5, wherein the carbamate I or a salt or adduct thereof and the compound II are applied simultaneously together or separately, or in succession.

7. The method defined in claim 5, wherein the carbamate I or the salt or adduct thereof is applied at a rate of from 0.01 to 2.5 kg/ha.

8. The method defined in claim 5, wherein the anilide II is applied at a rate of from 0.01 to 10 kg/ha.

9. The method defined in claim 5, wherein the carbamate I or the salt or adduct thereof is applied at a rate of from 0.05 to 2.5 kg/ha.

10. The method defined in claim 5, wherein the carbamate I or the salt or adduct thereof is applied at a rate of from 0.1 to 1.0 kg/ha.

11. The method defined in claim 5, wherein the anilide II is applied at a rate of from 0.05 to 5 kg/ha.

12. The method defined in claim 5, wherein the anilide II is applied at a rate of from 0.05 to 2 kg/ha.

13. The method defined in claim 5, wherein the composition is applied to seeds at a rate of from 0.001 to 250 g per kg of the seeds.

* * * * *